(12) United States Patent
Heinonen et al.

(10) Patent No.: US 6,295,506 B1
(45) Date of Patent: Sep. 25, 2001

(54) MEASUREMENT APPARATUS

(75) Inventors: Pekka Heinonen; Harri Okkonen, both of Espoo; Jukka Berg, Oulu, all of (FI)

(73) Assignee: Nokia Mobile Phones Limited, Espoo (FI)

( * ) Notice: Subject to any disclaimer, the term of this patent is extended or adjusted under 35 U.S.C. 154(b) by 0 days.

(21) Appl. No.: 09/178,313

(22) Filed: Oct. 23, 1998

(30) Foreign Application Priority Data

Oct. 27, 1997 (FI) ......................................................... 974065

(51) Int. Cl.$^7$ ............................................................... A61B 5/00
(52) U.S. Cl. ............................................. 702/104; 600/301
(58) Field of Search ................................... 702/104, 30, 31; 379/106.02; 340/501; 600/301, 316

(56) References Cited

U.S. PATENT DOCUMENTS

| | | | |
|---|---|---|---|
| 4,706,207 | 11/1987 | Hennessy et al. | 364/555 |
| 5,174,963 | 12/1992 | Fuller et al. | 422/82.05 |
| 5,307,263 * | 4/1994 | Brown | 364/413.09 |
| 5,507,288 | 4/1996 | Bocker et al. | 128/633 |
| 5,772,586 * | 6/1998 | Heinonen et al. | 600/300 |
| 5,802,465 | 9/1998 | Hamalainen et al. | 455/403 |
| 5,809,115 | 9/1998 | Inkinen | 379/93.05 |
| 5,840,020 * | 11/1998 | Heinonen et al. | 600/309 |
| 5,872,713 * | 2/1999 | Douglas et al. | 364/413.09 |
| 5,878,376 * | 3/1999 | Schurr | 702/102 |
| 5,899,855 * | 5/1999 | Brown | 600/301 |
| 6,106,780 * | 8/2000 | Douglas et al. | 422/58 |
| 6,122,536 * | 9/2000 | Sun et al. | 600/341 |
| 6,168,563 * | 1/2001 | Brown | 600/301 |

FOREIGN PATENT DOCUMENTS

| | | |
|---|---|---|
| 0 387 630 A3 | 9/1990 | (EP) . |
| 0 796 588 A1 | 9/1997 | (EP) . |
| 0 807 805 A2 | 11/1997 | (EP) . |
| 2 727 850 A1 | 6/1996 | (FR) . |
| WO 96/07908 | 3/1996 | (WO) . |
| WO 97/08544 | 3/1997 | (WO) . |
| WO 97/28737 | 8/1997 | (WO) . |
| WO 97/29847 | 8/1997 | (WO) . |

OTHER PUBLICATIONS

Finnish Office Action.
Patent Abstracts of Japan JP 06350726 A.
PCT International Search Report.

* cited by examiner

*Primary Examiner*—Patrick Assouad
(74) *Attorney, Agent, or Firm*—Perman & Green, LLP

(57) ABSTRACT

A system for measuring the blood glucose level in a sample of a patient's blood. Consumable test strips (5) are provided together with a code (7) which identifies the manufacturing batch of the strip (5). A measurement unit (2) is provided and is coupled to a mobile telephone (1). The measurement unit (2) is arranged to receive a test strip (5) and to determine a color change in a reagent (4) due to reaction of the reagent (4) with a blood sample. The identification code (7) is read at the same time by the measurement unit (3) and is transmitted by the mobile telephone (1) to a central database (9) provided by the test strip manufacturer. The database (9) contains identification codes (7) together with associated calibration data. Upon receipt of an identification code (7), the remote database (9) transmits the associated calibration data to the mobile telephone (1) which uses the calibration data to calculate a test result from the measured change in color. The result can be displayed to the patient on a display of the telephone (1).

11 Claims, 2 Drawing Sheets

MEASUREMENT APPARATUS

FIELD OF THE INVENTION

The present invention relates to measurement apparatus and in particular to measurement apparatus which makes use of a consumable reagent in a measuring process.

BACKGROUND OF THE INVENTION

There are many examples of measurement apparatus which make use of a consumable reagent as part of a measuring process. Consumable reagents are generally of a chemical, biochemical, or biological nature. One example of such an apparatus is a blood glucose meter designed to measure the level of glucose in a sample of a patient's blood. A small amount of a suitable reagent is printed or otherwise deposited onto an elongate plastic strip which can be inserted into the blood glucose meter. The meter comprises a reflectometry based measuring system which detects a change in the color of the printed reagent due to a reaction between the active reagent and glucose present in the blood sample.

It will be appreciated that in the case of a blood glucose meter, where a patient determines an insulin treatment regime on the basis of blood glucose measurements, the accuracy of the meter is critical. This requires very precise calibration of the meter. Initial calibration of the meter is normally carried out during and immediately following manufacturing, with certain calibration data being stored in permanent memory of the meter. However, calibration of the meter at this stage cannot easily account for changes and variations in the properties of the consumable reagents themselves, variations which might arise due to slight changes in the manufacturing process of the reagent and the test strip, environmental factors such a temperature and humidity, and changes in the property of the reagent over time.

It is known to provide blood glucose test strips, or rather a pack of such test strips, with a machine readable memory in which calibration data is stored. When a new pack of test strips is opened, the machine readable memory is read by the meter and calibration data downloaded into the memory of the blood glucose meter. In this way it is possible to take account of reagent manufacturing variations in the calibration of the meter. However, it will be appreciated that providing a machine readable memory with each packet of test strips is relatively expensive both in terms of the hardware required and in terms of the additional time required to program the memory during the manufacturing process.

In addition, it remains difficult to account for changes in the properties of a reagent over time. At best, only a poor estimate can be made based upon some predetermined criteria and only then if the age of the reagent is known. As such, manufacturers of blood glucose test strips tend to supply test strips in very limited numbers and make tight specifications for storage and lifetime to ensure that the properties of the reagents remain within desired limits. These specifications tend to work against economies of scale in the manufacturing and distribution of test strips.

These problems are not limited to blood glucose test strips and apply equally to other fields in which consumable reagents are used.

SUMMARY OF THE INVENTION

According to a first aspect of the present invention there is provided a measurement system comprising:

measurement apparatus for measuring a physical parameter using a consumable reagent, said reagent having an identification code associated therewith;

automatic telephone answering means;

a database coupled to the automatic telephone answering means and containing a set of consumable reagent identification codes and respective calibration data;

means for coupling the measurement apparatus to the automatic telephone answering means via a telephone link, the automatic telephone answering means being arranged to receive an identification code transmitted from the measurement apparatus over said telephone link, to subsequently access said database to identify the calibration data associated with said transmitted identification code, and to either transmit the identified calibration data to the measurement apparatus, or to calculate a test result using the identified calibration data and transmit the test result to the measurement apparatus.

By storing the calibration data for specific consumable reagents at a central database, it is possible to update the calibration data to reflect changes which may occur to the consumable reagents over time. Furthermore, it is no longer necessary to supply the calibration data to the end user with the reagents. This simplifies the manufacturing process and also eliminates the need to supply complex memory means to the end user.

A further advantage of the present invention is that data generated by the measurement apparatus using the consumable reagent can be transmitted to the central database where information from many apparatus can be collected and analysed.

In one embodiment of the present invention, the automatic telephone answering means is arranged to transmit calibration data associated with the received identification code back to the measurement apparatus. The measurement apparatus comprises data processing means for processing said measured physical parameter, using the received calibration data, to provide a test result. Preferably, the measurement apparatus comprises a display for displaying the test result to a user.

In an alternative embodiment of the present invention, the measurement apparatus is arranged to transmit said measured physical parameter to the automatic telephone answering means together with said identification code. The system further comprises data processing means, coupled to the database and the automatic telephone answering means, for calculating a test result using the identified calibration data and the received physical parameter. The automatic telephone answering means is arranged to transmit the test result back to the measurement apparatus, e.g. for display on a display of the apparatus. An advantage of this embodiment is that it is possible to use relatively complex algorithms to compute the test result due to the relatively high processing capability which can be provided at a central facility. Furthermore, the algorithm can be easily updated or modified.

Preferably, the identification code is provided with the consumable reagent in a machine readable form. For example, the code may be contained in a bar-code or in a solid state memory. The measurement apparatus is provided with a machine reader which is capable of reading the identification code into a memory of the measurement apparatus. An identification code may be provided with each individual consumable reagent or may be provided with a batch of such units. Where the consumable reagents are provided on a test strip, the code may be provided on one such test strip or on a dummy strip.

In an alternative embodiment, the identification code is provided in a human readable form. The measurement apparatus comprises a user interface for allowing the user to enter the identification code. For example, the user interface may be a keypad.

The measurement apparatus may comprise mobile telephone apparatus which is able to connect the measurement apparatus to the database via a wireless transmission channel. A measurement unit of the apparatus may be integral with said mobile phone or may be connectable thereto. Data may be transmitted between the mobile telephone apparatus and the automatic telephone answering means via a data call. In the case that the mobile telephone apparatus is a digital telephone apparatus according to the GSM system, the data may be transmitted using the short messaging system (SMS).

The present invention is applicable, for example, to a system for measuring the glucose level in a sample of a patient's blood.

According to a second aspect of the present invention there is provided a consumable reagent, or a pack of consumable reagents, in combination with an identification code, said reagent(s) being for use with the measurement system of the above first aspect of the present invention, where said identification code identifies a set of calibration data stored in said database.

Preferably, the combination of the second aspect of the present invention comprises a machine readable memory by means of which said identification code is stored. The memory may be a bar code, memory chip, magnetic strip, or any other suitable means.

According to a third aspect of the present invention there is provided a method of deriving a test result from a physical parameter measured using a measurement apparatus and a consumable reagent, the method comprising;

providing a consumable reagent together with an identification code;

providing a database containing a set of identification codes and respective calibration data;

transmitting said identification code from the measurement apparatus to the database via a telephone link; and automatically responding to receipt of the transmitted identification code by identifying the corresponding calibration data in the database, and transmitting that data, or a test result determined using the data, back to the measurement apparatus.

Preferably, said telephone link comprises a mobile telephone link, wherein the measurement apparatus comprises a measurement unit coupled to mobile telephone apparatus.

BRIEF DESCRIPTION OF THE DRAWINGS

For a better understanding of the present invention and in order to show how the same may be carried into effect reference will now be made, by way of example, to the accompanying drawings, in which.

DETAILED DESCRIPTION

Figure 1:
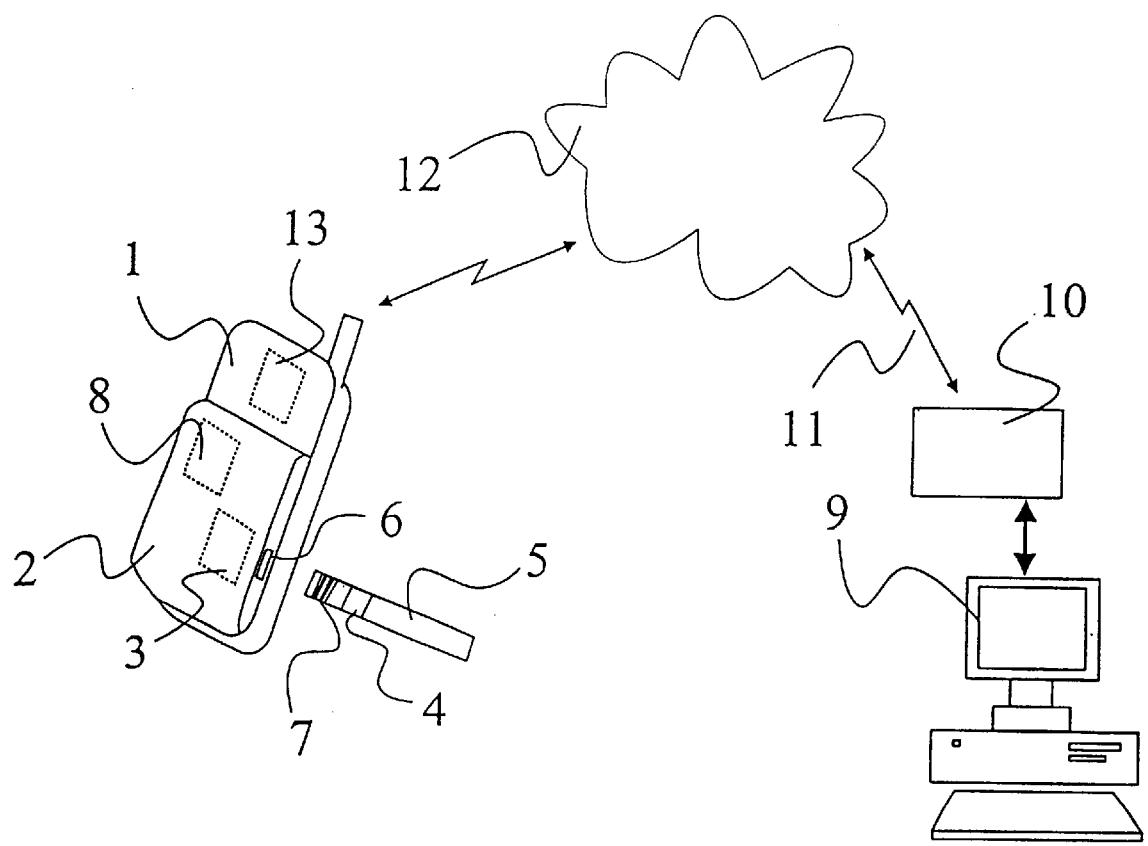
FIG. 1 shows a measurement system embodying the present invention.

There is shown in FIG. 1 a system which is capable of providing a diabetic patient with a blood glucose level test result. The system comprises a mobile telephone 1 which is shown from the rear in FIG. 1 and in which the keyboard and display are not visible. The telephone comprises modified software but is otherwise conventional. However, in place of the conventional battery, a measurement unit 2 is provided which can be inserted into the slot on the rear of the mobile phone 1 normally occupied by the battery. The measurement unit 2 contains a reduced size battery unit (not shown) for powering the measurement unit 2 and the phone 1.

The measurement unit 2 contains an internally arranged reflectometry system 3 which is operable to measure the color change in a consumable reagent 4 relative to some predetermined base level. The consumable reagent 4 is printed, or otherwise deposited, on a surface region of an elongate test strip 5. The test strip 5 is insertable into a slot 6 provided in the side of the measurement unit 2 and which provides access to the reflectometry system 3.

In addition to the consumable reagent 4, the test strip 5 is provided with a barcode 7 printed on its upper surface. The barcode 7 represents an identification code which identifies the manufacturing batch number of the test strip 5. The measurement unit 2 contains an optical reader, aligned with the slot 6, which reads the barcode 7 when the test strip 5 is inserted into the slot 6. The optical reader may be an independent internal component of the measurement unit 2, but is preferably provided, at least in part, by the reflectometry system 3. In either case, the read identification code is stored in a memory 8 of the measurement unit 2 or of the telephone 1.

The manufacturer or distributor of the test strips 5 maintains a central database 9 containing a set of identification codes, each of which uniquely identifies an individual manufacturing batch of test strips 5. Associated with each identification code is a set of calibration data. This calibration data typically includes an offset value and a scaling factor which can be used to relate a measured color change to a blood glucose level (non-linear calibration data may also be provided). Calibration data for a batch of test strips is initially determined following manufacture of a batch, for example by comparing the results of a test carried out using a typical measurement unit and by laboratory analysis. The calibration data however is updated at regular time intervals by re-testing samples taken from a retained test strip stock.

An automatic telephone answering device 10 is located at the manufacturer's (or distributor's) premises and is coupled to both a telephone line 11 and to the database 9. The operation of this device 10 is described below.

To initiate a blood glucose test, the patient activates a measurement sequence using a menu displayed on the phone's display. The patient then deposits a small amount of blood on top of the reagent 4. After a short time, the test strip 5 is fully inserted into the slot 6. Upon insertion, the identification code conveyed by the barcode 7 is read into the unit's memory 8. The color change in the reagent 4 is then determined by the reflectometry system 3 and the result also read into the unit's memory 8.

The patient is then prompted, by a message displayed on the telephone's display, to initiate a data call to the remote automatic telephone answering device 10. Following acceptance of the prompt by the user, the telephone 1 opens a data channel with a cellular telephone 12 network and transmits the read identification code to the automatic telephone answering device 10 via the telephone line 11. The answering device 10 responds by accessing the database 9 and downloading therefrom the calibration data corresponding to the received identification code. The answering device 10 then formats the calibration data and transmits it back to the mobile telephone 1 via the cellular network 12.

The calibration data received by the telephone 1 is stored in the memory 8. The telephone then proceeds to calculate a blood glucose test result using the measured color change, the received calibration data, and a calculation algorithm which is pre-stored in the measurement unit's memory 8. This calculation is carried out by a central processing unit 13 of the phone 1.

Figure 2:
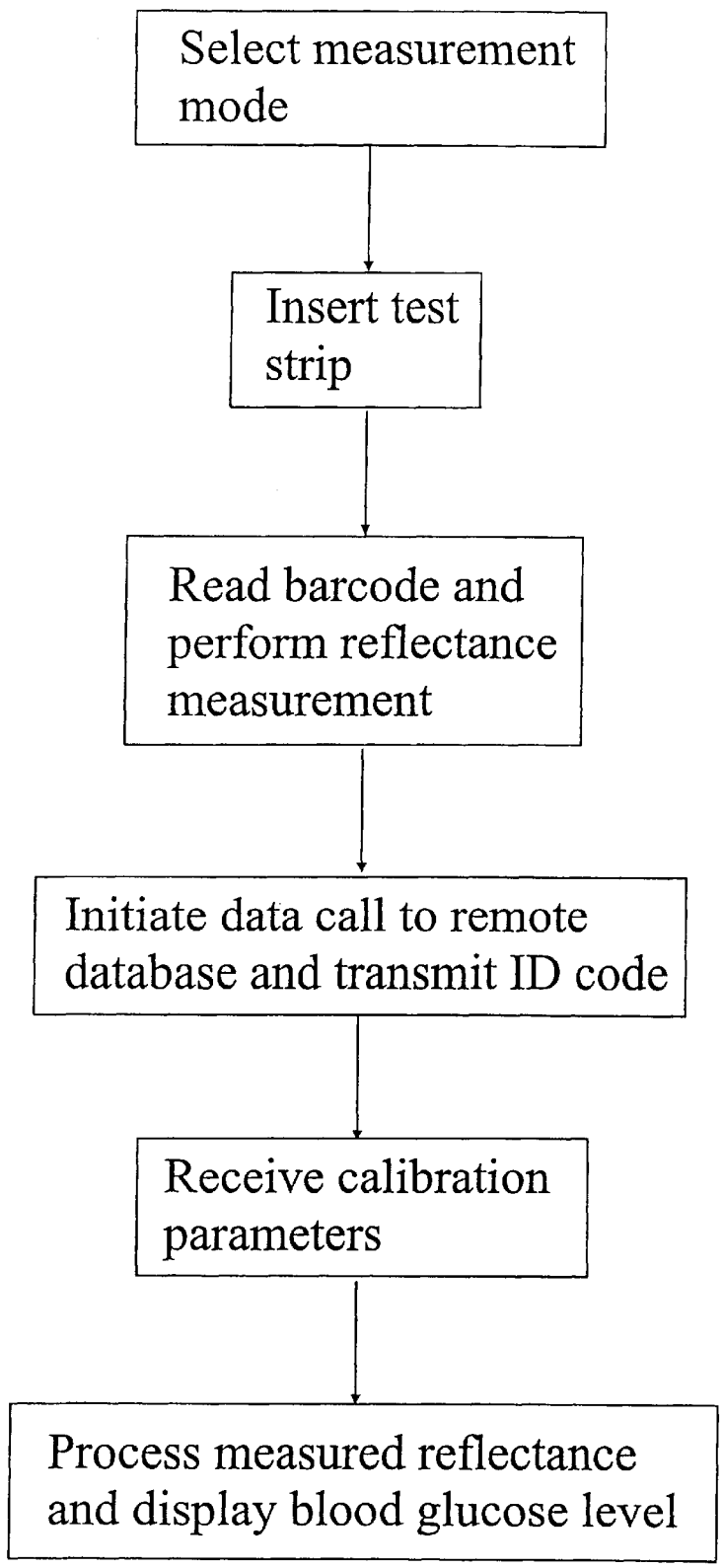
FIG. 2 is a flow diagram illustrating a measurement method implemented by the system of FIG. 1.

The main steps associated with the measurement process at the measurement apparatus are shown in the flow diagram of FIG. 2.

It will be appreciated that the same result can be obtained by transmitting the measured color change from the measurement unit 2 and the mobile telephone 1, to the remote database 9, together with the identification code. The database 9 can then process the measured value using the calibration data to generate a test result. It is then not necessary to transmit the calibration data to the measurement unit 2 and only the test result needs to be transmitted. The result received by the mobile telephone 1 can then be displayed directly on the telephone's display.

In addition to providing the measurement unit with the most up to date calibration data, the system described above provides a number of other significant advantages. For example, if a user mistakenly tries to use a test strip which has passed its 'use by' date, the user can be notified of this, and the measurement blocked, by the database and the automatic answering device. Accurate records can also be kept, by the database, of the usage pattern of test strips.

It will be appreciated that modifications may be made to the above described embodiment without departing from the scope of the present invention. For example, whilst the embodiment described above makes use of a mobile telephone, alternative embodiments may use land line telephones or two-way pagers.

What is claimed is:

1. A measurement system comprising:
    measurement apparatus for measuring a physical parameter using a consumable reagent, said reagent having an identification code associated therewith;
    automatic telephone answering means;
    a database coupled to the automatic telephone answering means and containing a set of consumable reagent identification codes and respective calibration data;
    means for coupling the measurement apparatus to the automatic telephone answering means via a telephone link,
    the automatic telephone answering means being arranged to receive an identification code transmitted from the measurement apparatus over said telephone link, to subsequently access said database to identify the calibration data associated with said transmitted identification code, and to either transmit the identified calibration data to the measurement apparatus, or to calculate a test result using the identified calibration data and transmit the test result to the measurement apparatus.

2. A system according to claim 1, wherein the automatic telephone answering means is arranged to transmit calibration data associated with the received identification code back to the measurement apparatus and the measurement apparatus comprises data processing means for processing said measured physical parameter, using the received calibration data, to provide a test result.

3. A system according to claim 1, wherein the measurement apparatus is arranged to transmit said measured physical parameter to the automatic telephone answering means together with said identification code, the system further comprising data processing means, coupled to the database and the automatic telephone answering means, for calculating a test result using the identified calibration data and the received physical parameter, the automatic telephone answering means being arranged to transmit the test result back to the measurement apparatus.

4. A system according to claim 1, wherein the identification code is provided with the consumable reagent in a machine readable form.

5. A system according to claim 4, wherein the identification code is contained in a bar-code or in a solid state memory and the measurement apparatus is provided with a machine reader which is capable of reading the identification code into a memory of the measurement apparatus.

6. A system according to claim 1, wherein the measurement apparatus comprises mobile telephone apparatus which is able to connect the measurement apparatus to the database via a wireless transmission channel.

7. A system according to claim 1, wherein the measurement apparatus is arranged to provide a measure of the glucose level in a sample of a patient's blood.

8. A consumable reagent, or a pack of consumable reagents, in combination with an identification code, said reagent(s) being for use with the measurement system of claim 1, where said identification code identifies a set of calibration data stored in said database.

9. The combination of claim 5, comprising a machine readable memory by means of which said identification code is stored.

10. A method of deriving a test result from a physical parameter measured using a measurement apparatus and a consumable reagent, the method comprising;
    providing a consumable reagent together with an identification code;
    providing a database containing a set of identification codes and respective calibration data;
    transmitting said identification code from the measurement apparatus to the database via a telephone link; and
    automatically responding to receipt of the transmitted identification code by identifying the corresponding calibration data in the database, and transmitting that data, or a test result determined using the data, back to the measurement apparatus.

11. A method according to claim 10, said telephone link comprising a mobile telephone link, wherein the measurement apparatus comprises a measurement unit coupled to mobile telephone apparatus.

* * * * *